US010617373B2

(12) United States Patent
Ahn et al.

(10) Patent No.: US 10,617,373 B2
(45) Date of Patent: Apr. 14, 2020

(54) DENTAL X-RAY RADIOGRAPHING APPARATUS HAVING RADIOGRAPHING UNIT HOUSING

(71) Applicants: VATECH Co., Ltd., Gyeonggi-do (KR); VATECH EWOO Holdings Co., Ltd., Gyeonggi-do (KR)

(72) Inventors: Byung Jun Ahn, Gyeonggi-do (KR); Jung In Lee, Gyeonggi-do (KR); Yeong Kyun Kim, Gyeonggi-do (KR); Chi Taek Oh, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 452 days.

(21) Appl. No.: 15/526,679

(22) PCT Filed: Nov. 12, 2015

(86) PCT No.: PCT/KR2015/012172
§ 371 (c)(1),
(2) Date: May 12, 2017

(87) PCT Pub. No.: WO2016/076643
PCT Pub. Date: May 19, 2016

(65) Prior Publication Data
US 2017/0319158 A1   Nov. 9, 2017

(30) Foreign Application Priority Data
Nov. 12, 2014 (KR) .................. 10-2014-0156980
Oct. 26, 2015 (KR) .................. 10-2015-0148993

(51) Int. Cl.
*A61B 6/14*    (2006.01)
*A61B 6/04*    (2006.01)
(Continued)

(52) U.S. Cl.
CPC .............. *A61B 6/14* (2013.01); *A61B 6/03* (2013.01); *A61B 6/0428* (2013.01);
(Continued)

(58) Field of Classification Search
CPC .. A61B 6/00; A61B 6/03; A61B 6/035; A61B 6/0428; A61B 6/14; A61B 6/4435; A61B 6/4452; A61B 6/547
See application file for complete search history.

(56) References Cited

U.S. PATENT DOCUMENTS 3,974,388 A * 8/1976 Distler ................ A61B 6/0457
378/20
4,599,739 A 7/1986 Nishikawa et al.
(Continued)

FOREIGN PATENT DOCUMENTS

KR    10-2009-0053768 A     5/2009
KR    10-2009-0130719 A    12/2009
(Continued)

OTHER PUBLICATIONS

European Patent Office, Extended European Search Report of corresponding EP Patent Application No. 15859487.9, dated May 28, 2018.

*Primary Examiner* — Chih-Cheng Kao
(74) *Attorney, Agent, or Firm* — IP Legal Services, LLC

(57) ABSTRACT

Disclosed is a dental X-ray imaging apparatus having a radiographing housing so as to provide a stable radiographing environment to an examinee. The dental X-ray radiographing apparatus includes a radiographing unit including a rotary arm, an X-ray generator, and an X-ray sensor, and a radiographing housing for covering an upper part, an outside and an inside of an operating range of the radiographing unit. The imaging apparatus further includes a lifter configured to move the radiographing housing, and a handle frame disposed at a lower part of the radiographing (Continued)

housing with a variable height and including a chin rest, wherein the lifter moves the radiographing housing such that the distance between the chin rest and the radiographing housing is constant.

15 Claims, 8 Drawing Sheets

(51) Int. Cl.
  *A61B 6/03* (2006.01)
  *A61B 6/00* (2006.01)
(52) U.S. Cl.
  CPC .......... *A61B 6/4435* (2013.01); *A61B 6/4452* (2013.01); *A61B 6/035* (2013.01); *A61B 6/547* (2013.01)

(56) References Cited

U.S. PATENT DOCUMENTS

| | | | |
|---|---|---|---|
| 6,118,842 A * | 9/2000 | Arai | A61B 6/032 378/38 |
| 2002/0085666 A1 * | 7/2002 | Molteni | A61B 6/04 378/38 |
| 2005/0254621 A1 | 11/2005 | Kalender et al. | |
| 2008/0298554 A1 * | 12/2008 | Tacconi | A61B 6/032 378/196 |
| 2011/0129058 A1 * | 6/2011 | Ulrici | A61B 6/14 378/4 |
| 2011/0194670 A1 * | 8/2011 | Borghese | A61B 5/0064 378/25 |
| 2012/0243762 A1 | 9/2012 | Kanerva et al. | |
| 2013/0070894 A1 * | 3/2013 | Tonami | A61B 6/037 378/37 |
| 2014/0126687 A1 | 5/2014 | Yoshikawa et al. | |
| 2014/0205074 A1 | 7/2014 | Gregerson et al. | |
| 2014/0254750 A1 | 9/2014 | Yoshimura et al. | |
| 2015/0206614 A1 | 7/2015 | Roh et al. | |
| 2015/0230766 A1 | 8/2015 | Wang et al. | |
| 2015/0289827 A1 | 10/2015 | Laukkanen et al. | |
| 2016/0213336 A1 | 7/2016 | Kim et al. | |

FOREIGN PATENT DOCUMENTS

| | | |
|---|---|---|
| KR | 10-2010-0115000 A | 10/2010 |
| KR | 10-2011-0050656 A | 5/2011 |
| KR | 10-2012-0107438 A | 10/2012 |
| KR | 10-2013-0003259 A | 1/2013 |
| KR | 10-2015-0024706 A | 3/2015 |
| KR | 10-2015-0062521 A | 6/2015 |
| KR | 10-2015-0086693 A | 7/2015 |
| WO | 2014/047518 A1 | 3/2014 |
| WO | 2014/080083 A1 | 5/2014 |

* cited by examiner

DENTAL X-RAY RADIOGRAPHING APPARATUS HAVING RADIOGRAPHING UNIT HOUSING

CROSS REFERENCE TO RELATED APPLICATIONS

This application is a National Stage Patent Application of PCT International Patent Application No. PCT/KR2015/012172 (filed on Nov. 12, 2015) under 35 U.S.C. § 371, which claims priority to Korean Patent Application Nos. 10-2014-0156980 (filed on Nov. 12, 2014) and 10-2015-0148993 (filed on Oct. 26, 2015), the teachings of which are incorporated herein in their entireties by reference.

TECHNICAL FIELD

The present invention relates to an X-ray radiographing apparatus. More particularly, the present invention relates to a dental X-ray radiographing apparatus in which an X-ray generator and an X-ray sensor rotates around a head of an examinee to radiograph an X-ray radiograph.

BACKGROUND ART

X-ray radiographing is a radiation radiographing method using the penetrative characteristic of X-rays, and image information of an internal structure of the target is provided based on the accumulated extent of attenuation in a process of penetrating through the target. An X-ray radiographing apparatus for this include: an X-ray generator radiating X-rays, an X-ray sensor disposed to face the X-ray generator with a target interposed therebetween and detecting X-rays that have passed the target, and an image-processing device implementing an X-ray radiograph using the detection result of the X-ray sensor. Meanwhile, recently, due to developments in semiconductor and data processing technologies, X-ray radiographing has been rapidly replaced with Digital Radiography (DR) using a digital detector, and radiographing methods have been improved in various ways.

FIG. 1 shows a conventional dental X-ray radiographing apparatus.

The conventional dental X-ray radiographing apparatus includes a base supported by the floor, a column vertically standing from the base, and a lifter 10 vertically moving along the column in accordance with a height of the target. The lifter 10 is connected to a cantilever 20 at one side thereof. The cantilever 20 is connected to a rotary arm 30 at a lower part thereof so that the rotary arm 30 may rotate. The rotary arm 30 includes a generator 31 disposed on one side thereof with a rotation axis interposed therebetween, and an X-ray sensor 32 disposed opposite the generator 31 and opposite to the rotation axis. An examinee's head that includes a dental arch 50 of the examinee is fixedly disposed around a rotation axis 25C, and a position thereof may be adjusted depending on the area requiring examination.

A rotation driver 25 is provided to connect the rotary arm 30 and the cantilever 20 by being disposed therebetween, and to rotate the rotary aim 30 about the rotation axis 25C using driving power. The rotation driver 25 rotates the rotary arm 30 to a desired angle when radiographing a panoramic radiograph of the dental arch 50 of the examinee or when radiographing various X-ray radiographs to obtain a CT image.

Panoramic X-ray radiographs that are provided by using such a dental X-ray radiographing apparatus are used as the most familiar standard image to dentists since the overall arrangement relationship of teeth and surrounding tissues may be easily grasped from the images. X-ray CT radiographs may display a 3D image of the examinee and accurately and clearly display tomographic radiographs according to a user's desired position and direction, and thus X-ray radiographs have con to be utilized in fields requiring high precision, such as an implant procedure. Recently, in the field of orthodontics and the like, the utilization of the X-ray 3D radiographs is increasing.

In order to reconfigure panoramic X-ray radiographs, X-ray tomographic radiographs, or X-ray 3D radiographs, a dental X-ray radiographing apparatus requires a large number of x-ray transmission radiographs taken at various angles of the examinee. Therefore, a rotation amount of the rotary arm 30 for rotating the generator 31 and the X-ray sensor 32 increases, and a speed of rotation is also increased for rapid radiographing. However, operations during sequential X-ray radiographing cause the examinee to feel uneasy. Thus, motion artifacts may be generated. In addition, since the operation range of a radiographing apparatus is wide and the apparatus is not clearly distinguished from the surroundings, it is difficult to utilize the space.

DISCLOSURE

Technical Problem

An object of the present invention is to provide a dental X-ray radiographing apparatus including a radiographing housing that covers the whole radiographing unit including a generator, an X-ray sensor, and a rotary arm and provides a stable radiographing environment to an examinee.

Another object of the present invention is to provide a dental X-ray radiographing apparatus, while providing the radiographing housing, that minimizes a rotation range of the radiographing unit while ensuring a radiographing target area of a required size since there is a concern that the radiographing housing occupies an excessively large space in order to cover the maximum radius of rotation of the radiographing unit.

In addition, still another object of the present invention is to provide a dental X-ray radiographing apparatus in which the radiographing housing is quickly and conveniently moved to a corresponding position when an examinee is positioned for radiographing.

In addition, still another object of the present invention is to provide a dental X-ray radiographing apparatus capable of preventing a radiographing housing from being deflected or vibrated by allowing a load of the radiographing housing to be distributed and supported.

Technical Solution

In order to accomplish the above object, according to the present invention, there is provided a dental X-ray radiographing apparatus, the apparatus including: a radiographing unit including a X-ray generator and an X-ray sensor that rotate about a vertical rotation axis with a target interposed therebetween; and a radiographing housing being opened at a lower part thereof and being closed at an upper part thereof, and providing a radiographing space receiving the target therein and covering the radiographing unit.

The radiographing space may have a conical shape such that a width thereof increases along a downward.

The X-ray sensor may be inclined with respect to the rotation axis such that a distance between the X-ray sensor and the rotation axis increases along a downward. The X-ray sensor may move in a tangential direction of a rotation track centered on the rotation axis during X-ray radiographing.

The dental X-ray radiographing apparatus according to the present invention may further include: a lifter that vertically moves the radiographing unit and the radiographing housing upward and downward. In addition, the apparatus may further include: a handle frame disposed at a lower part of the radiographing housing with a height thereof being variable. Herein, the target may a head of an examinee, and the apparatus may further include: a chin rest disposed on the handle frame to support a chin of the examinee. A height of the radiographing unit relative to the chin rest during X-ray radiographing may be constant. In addition, the apparatus may further include: a displacement measuring unit measuring a height of the handle frame; and a controller controlling a vertical movement of the lifter according to the height of the handle frame. In addition, the apparatus may further include: a positioning guide disposed on the handle frame to support the target, and the positioning guide being the entirely or partially received inside the radiographing space during X-ray radiographing.

The dental X-ray radiographing apparatus according to the present invention may further include: a positioning guide disposed on the handle frame to support the target, and the positioning guide being the entirely or partially received inside the radiographing space during X-ray radiographing. In addition, the apparatus may further include: at least one camera installed in the radiographing housing and imaging the target.

The radiographing unit may include a rotary arm connecting the X-ray generator and the X-ray sensor to each other, and rotating about the rotation axis. Herein, the dental X-ray radiographing apparatus according to the present invention may further include: a rotation support connecting the rotary arm and the radiographing housing. The rotation support may include a bearing disposed between the rotary arm and the radiographing housing. The rotation support may further include: a first bracket connected to the rotary arm and rotating therewith; and a second bracket connected to the radiographing housing with the bearing therebetween.

Meanwhile, in the dental X-ray radiographing apparatus according to the present invention, a radius of rotation of the X-ray sensor may be smaller than a radius of rotation of the X-ray generator.

Advantageous Effects

According to the present invention, there is provided a radiographing housing that covers the whole radiographing unit including a generator, an X-ray sensor, and a rotary arm so that a stable radiographing environment may be provided to an examinee.

In addition, according to the present invention, there is provided a dental X-ray radiographing apparatus that has a radiographing housing with a compact size by ensuring a radiographing target area of a required size and by minimizing the rotation range of a radiographing unit.

In addition, the present invention provides a dental X-ray radiographing apparatus in which a radiographing housing is configured to quickly and conveniently move to a corresponding position when an examinee is positioned for radiographing.

In addition, the present invention may prevent a radiographing housing from being deflected or vibrated by allowing a load of the radiographing housing to be distributed and supported.

MODE FOR INVENTION

Figure 1:
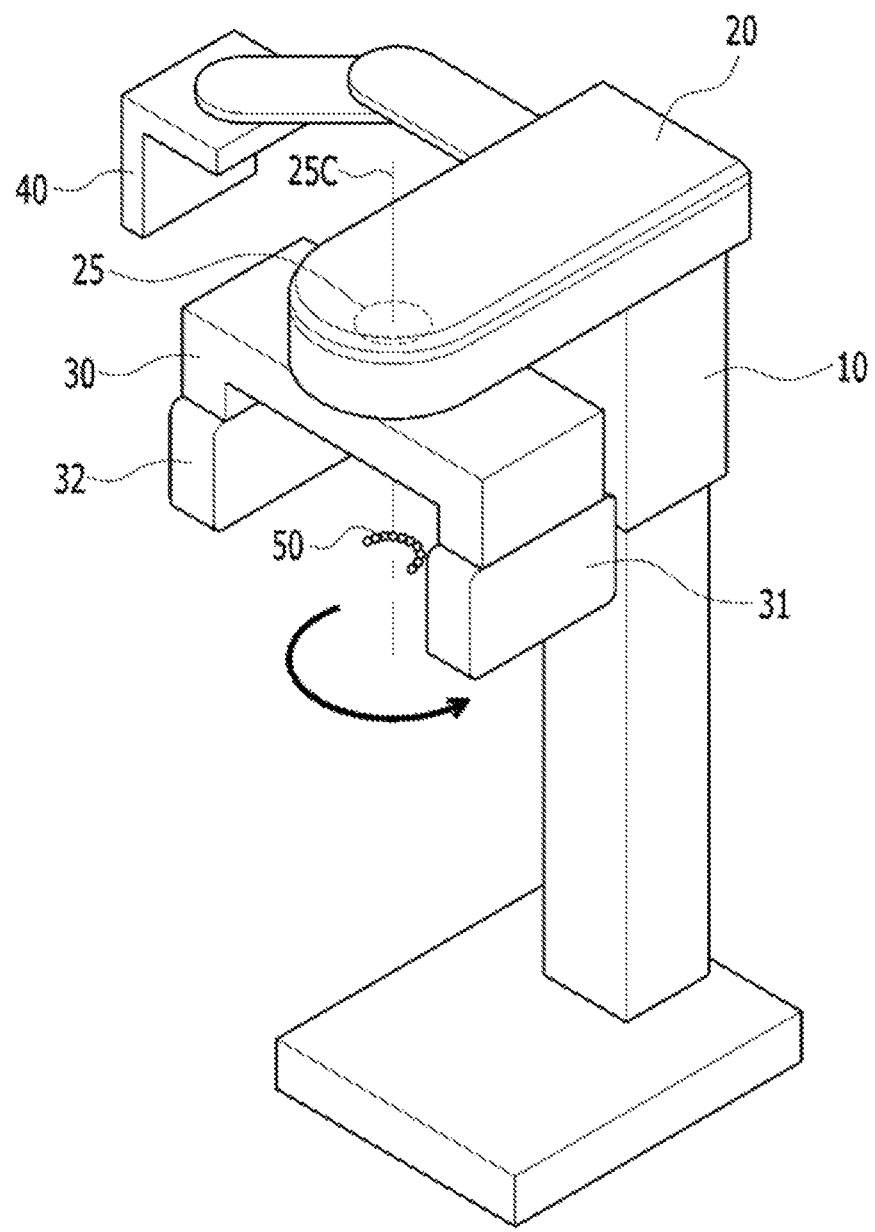
FIG. 1 shows a conventional dental X-ray radiographing apparatus.

Hereinbelow, exemplary embodiments of the present invention will be described in detail with reference to the accompanying drawings. The embodiments set forth herein are provided for illustrative purposes to fully convey the concept of the present invention. It will be apparent to a person skilled in the art that the present invention should not be construed to be limited to these embodiments. Throughout the drawings, the same reference numerals will refer to the same or like parts. Descriptions of some components depicted in a specific drawing will be omitted, when their reference numerals are identical to those of the components described with reference to another drawing.

Figure 2:
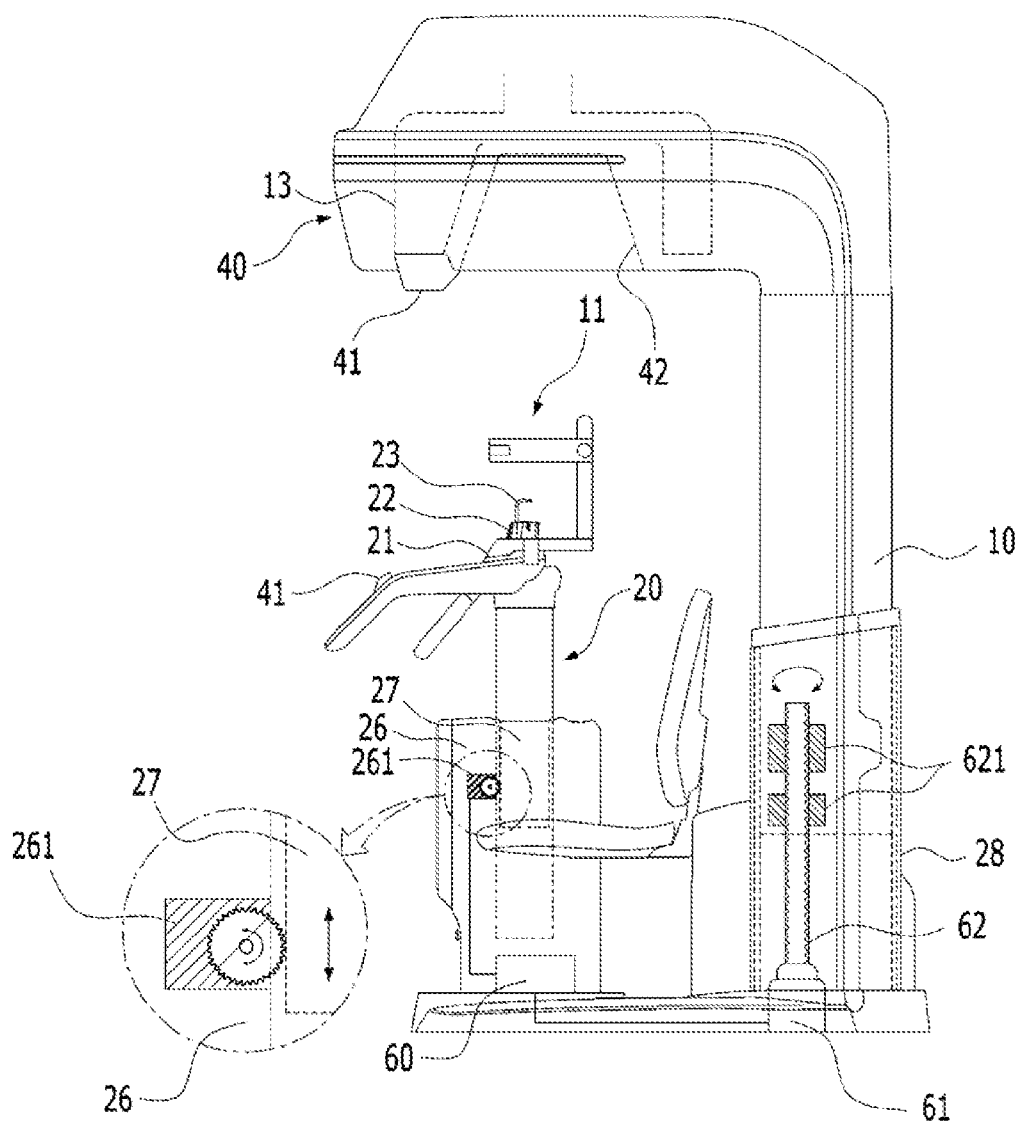
FIG. 2 shows the exterior and a schematic configuration of an X-ray radiographing apparatus according to one embodiment of the present invention.

FIG. 2 shows the exterior and a schematic configuration of an X-ray radiographing apparatus according to one embodiment of the present invention.

The X-ray radiographing apparatus according to the embodiment of the present invention includes a base frame 28 supported by being disposed on the floor, a lifter 10 installed to vertically move with a part thereof overlapping with the base frame 28, and a radiographing housing 40 extending from the lifter 10 to an upper part of an examinee chair. A positioning guide 11 and a chin rest 22 that fasten and support an examinee's head are arranged below the radiographing housing 40. The positioning guide 11 and the chin rest 22 are supported by a chin rest support 21. The chin rest support 21 is a part of a handle frame 20 and is installed, for example, in an upper part of the handle frame 20. A vertical column part 27 is provided in another part of the handle frame 20, for example, in a lower part thereof, and the vertical column part 27 is inserted into a handle frame base 26 that is fixed with respect to the base frame 28. The handle frame 20 may vertically move with respect to the handle frame base 26. Preferably, the handle frame 20 is installed to horizontally rotate.

First, the radiographing housing 40 will be described. A radiographing unit 13 is installed inside the radiographing housing 40. The radiographing unit 13 includes a rotation driver supported by an upper part of the radiographing housing 40, a rotary arm, and a sensor unit and a generator unit that are disposed on both sides of the rotary aim. Detailed configurations thereof will be described later. The radiographing housing 40 forms an exterior that covers the outer surface of a rotation range of the radiographing unit 13. In addition, the radiographing housing 40 covers an inner surface 42 of the rotation range of the radiographing unit 13 and provides a radiographing space into which a part or the entirety of the examinee's head is inserted during X-ray radiographing. At the same time, the radiographing housing 40 makes configuration components of the radiographing unit 13 invisible to the examinee. Accordingly, anxiety or reflexive movement of the examinee in response to the operation of the radiographing unit 13 may be prevented. As a result, motion artifacts in an X-ray radiograph may be prevented.

Herein, the inner surface 42 of the radiographing housing 40 of the X-ray radiographing apparatus according to the present embodiment may be parallel to an X-ray sensor, which will be described later. As a result, the distance between the inner surface 42 and the examinee's head increases along a direction from the top to the bottom. For example, the inner surface 42 may be inclined at a predetermined angle with respect to an imaginary vertical line so that a distance between the inner surface 42 and the imaginary vertical line increases along a downward direction. However, if the X-ray sensor is arranged parallel to a rotation axis of the radiographing unit, the radiographing housing 40 may include an inner surface that is perpendicular to the floor.

In addition, the X-ray radiographing apparatus according to the present embodiment may further include a number of cameras 41 that optically images an outside of an examinee's face from a lower part of the radiographing housing 40 and from an upper part of the handle frame 20. Accordingly, X-ray radiographs obtained by X-ray radiographing and face images obtained using the number of cameras 41 may be provided. Meanwhile, the present embodiment includes a chair as shown in the figure. When the examinee sits on the chair, the height of the handle frame 20 is adjusted so that the examinee comfortably sits on the chair while putting his or hers chin on the chin rest 22 and biting a bite block 23. Then, X-ray radiographing is performed when a part or the entire head of the examinee is inserted into the radiographing housing 40 by lowering the radiographing housing 40 including the radiographing unit 13 through the lifter 10.

Herein, during X-ray radiographing, a height of the radiographing unit 13 relative to the handle frame 20, more strictly relative to the chin rest 22, may be maintained constant.

For this, heights of the handle frame 20 and the radiographing housing 40 may set by interlocking with each other. As one example of the above configuration, a displacement measuring unit 261 that measures height variation according to the vertical movement of the vertical column part 27 may be provided inside the handle frame base 26. A potentiometer may be used for the displacement measuring unit 261. The displacement measuring unit 261 is connected to a controller 60, and the controller 60 is connected to an actuator 61 that vertically moves the lifter 10. The actuator 61 may be guided, for example, by a driving shaft 62 so as to move therewith, and may adjust the height of the lifter 10 by using a driving guide 621 that receives a vertically moving force. The driving guide 621 is fixed to the lifter 10.

As described above, the radiographing housing 40 may vertically move according to the operation of the lifter 10 before and after X-ray radiographing. As a result, although the height of the chin rest 22 varies according to the position of the examinee's head, the height of the radiographing unit 13 relative to the chin rest 22 is maintained constant during X-ray radiographing. In one embodiment, when the height of the head varies according to the height of the examinee, the chin rest 22 may be set at the position of the examinee's head by upwardly moving the handle frame 20. Then, the lifter 10 may be controlled such that the height of the radiographing unit 13 relative to the chin rest 22 is maintained constant since the radiographing housing 40 downwardly moves for X-ray radiographing. Accordingly, although examinees have different heights, a part or the entire head of the examinee is always placed at a predetermined position inside the radiographing housing 40. In addition, the radiographing housing 40 may not expose movements of configuration components that constitute the radiographing unit 13 to the examinee and to the outside. For this, the radiographing housing 40 includes an opaque casing for a closed top and perimeter thereof. In addition, the radiographing housing 40 may provide a cylindrical or conical radiographing space in which the examinee's head may be placed.

For reference, a dental X-ray radiographing apparatus according to the present invention may be configured without the chair, unlike the present invention, so that X-ray radiographing is performed while an examinee is standing. In the above case, the handle frame 20 may be disposed to match a given height while the examinee is standing.

Figure 3:
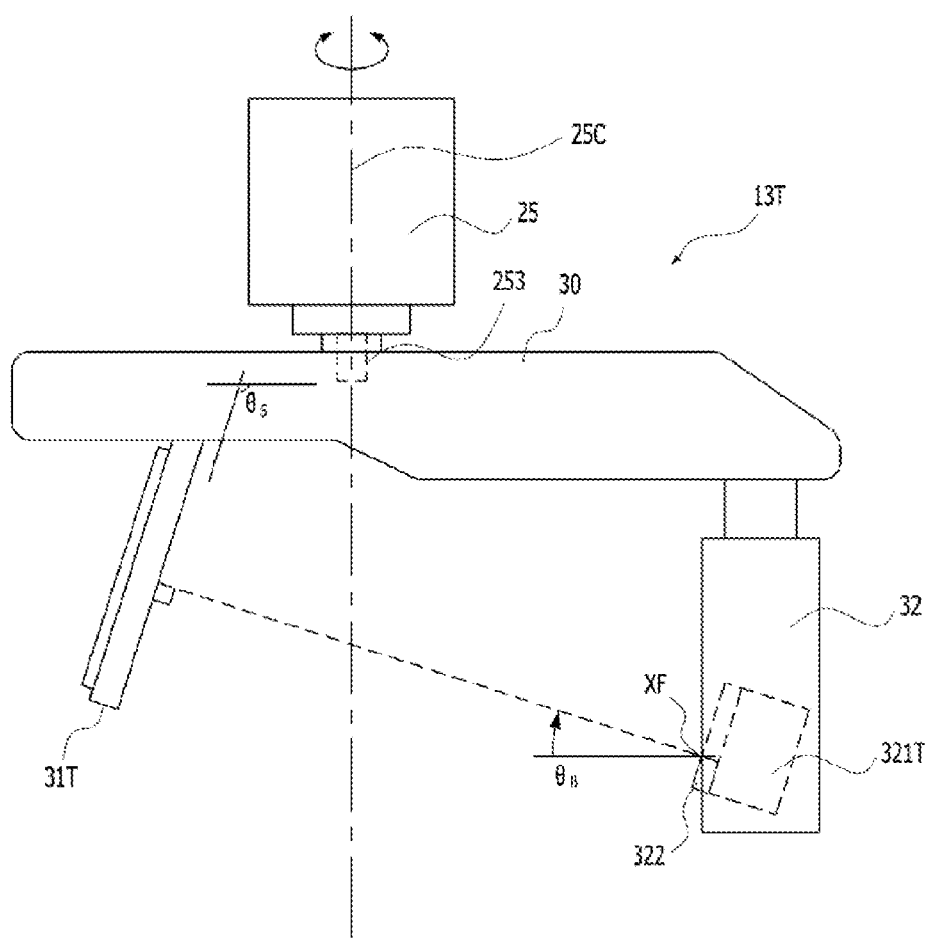
FIG. 3 shows a configuration of an X-ray radiographing unit according to one embodiment of the present invention.

FIG. 3 shows the configuration of an X-ray radiographing unit according to one embodiment of the present invention.

The radiographing unit 13T includes an rotation driver 25, a rotary arm 30 rotating around a rotation axis 25C by the rotation driver 25, an generator unit 32 arranged on one side of the rotary arm 30 and including an X-ray generator 321T and a collimator 322 to radiate collimated X-ray beams with a predetermined size, and a sensor unit 31T arranged on another side of the rotary arm 30 to face the generator unit 32 with a target interposed therebetween, and including a X-ray sensor that moves along the circumferential direction of the rotary arm 30 when the rotary arm 30 rotates, preferably along the tangential direction of a rotation track.

The X-ray generator 321T and the collimator 322 are installed such that a radiation direction of an X-ray beam, represented as a dotted line, forms a predetermined angle $\theta_B$ with respect to a surface that is perpendicular to the rotation axis 25C of the rotary arm 30 when viewed edge-on. The sensor unit 31T includes an X-ray sensor that is arranged to face the X-ray generator 321T and has a receiving surface which is inclined at a predetermined angle with respect to a surface that is parallel to the rotation axis 25C. Herein, a emitting direction of the generator is inclined from bottom to top with respect to the surface which is vertical to the rotation axis 25C. The predetermined angle $\theta_B$ may be $0°<\theta_B<90°$. More preferably, the predetermined angle $\theta_B$ may satisfy $0°<\theta_B<45°$. As a result, the sensor unit 31T is also downwardly inclined by an angle corresponding to $\theta_B$ with respect to the surface that is a virtual cylindrical outer circumferential surface around the rotation axis 25C and parallel to the rotation axis 25C. Accordingly, the sensor unit 31T has an angle $\theta_S$ of $90°<\theta_S<180°$ with respect to a surface in which rotary arm 30 is placed. More preferably, the sensor unit 31T may satisfy $90°<\theta_S 135°$. It is preferable for a central axis between the sensor unit 31T and the X-ray beam, that is, a virtual line that connects the minimum distance from an emission point XF of the X-ray generator 321T to the sensor unit 31T, to be perpendicular to the sensor unit 31T when viewed edge-on.

Since the radiation direction of the X-ray beam is inclined from bottom to top and the sensor unit 31T is downwardly inclined, a radiographing space inside the radiographing housing 40 is formed to have a conical shape with a wider lower part, as shown in FIG. 2. Thus, the examinee may place his or her head more conveniently.

Meanwhile, the present embodiment has a configuration in which a housing of the generator unit 32 is arranged to be perpendicular to the rotary arm 30 and the X-ray generator 321T is arranged to be inclined inside the housing. However, the generator unit 32 itself may be arranged to be inclined such that the generator unit 32 is approximately parallel to the sensor unit 31T.

The rotation driver 25 is connected to the lifter 10 and arranged inside of an upper part of the radiographing housing 40, and a driving axis 253 thereof is connected to the rotation axis 25C of the rotary arm 30. In one embodiment, the rotation driver 25 may include a direct operation motor known as a direct drive motor, and may be configured so that the center of the driving axis 253 matches the rotation axis 25C of the rotary aim 30. Herein, power wirings and signal wirings around the driving axis 253 may be connected by using slip rings to prevent cables from being twisted. The slip rings may be wireless slip rings having wireless contacts.

Figure 4:
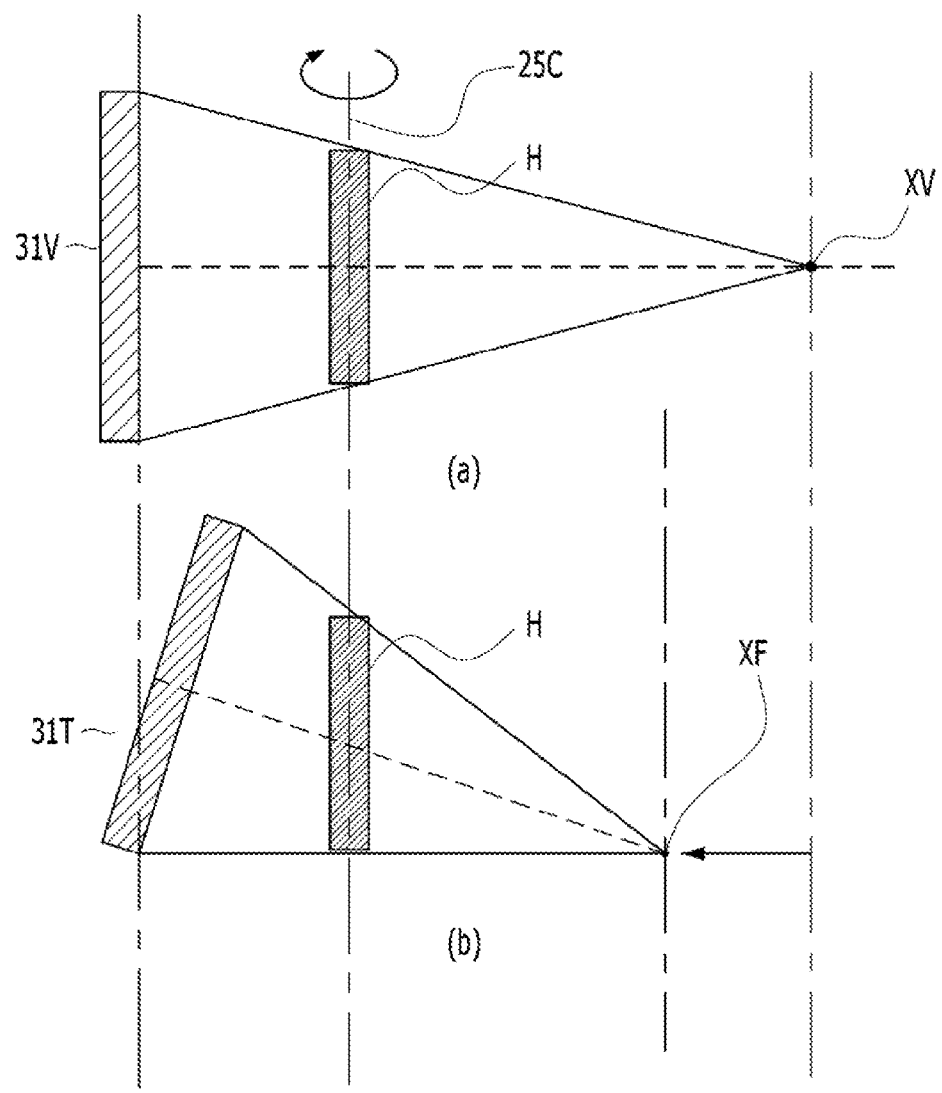
FIG. 4 shows a principle in which a rotation range of the radiographing unit is reduced on the assumption that the same size of target radiographing space is provided by a configuration of the radiographing unit according to a second embodiment of FIG. 3.

FIG. 4 shows the principle in which a rotation range of the radiographing unit is reduced on the assumption that the same size of radiographing target space is provided by a configuration of the radiographing unit according to a second embodiment of FIG. 3.

FIG. 4(a) shows the case similar to the conventional art, in which a radiation direction of an X-ray beam is parallel to a surface that is perpendicular to a rotation axis 25C, so that a sensor unit 31V is parallel to the rotation axis 25C, and FIG. 4(b) shows the case where the sensor unit 31T and the radiation direction of the X-ray beam are inclined as described with reference to FIG. 3 according to the present invention.

Herein, the height H of a radiographing examinee is the same in FIGS. 4(a) and 4(b). In FIG. 4(b), an X-ray beam is obliquely radiated and the sensor unit 31T is installed to be inclined, thus an emission point XF of the X-ray beam is positioned relatively closer to the rotation axis 25C than an emission point XV of FIG. 4(a). This means that a rotation range of the radiographing unit may be narrowed by a difference in distance between the two emission points XF and XV. Accordingly, a space occupied by an X-ray radiographing unit may be reduced, and more directly, the size of the radiographing unit described above may be reduced.

Figure 5:
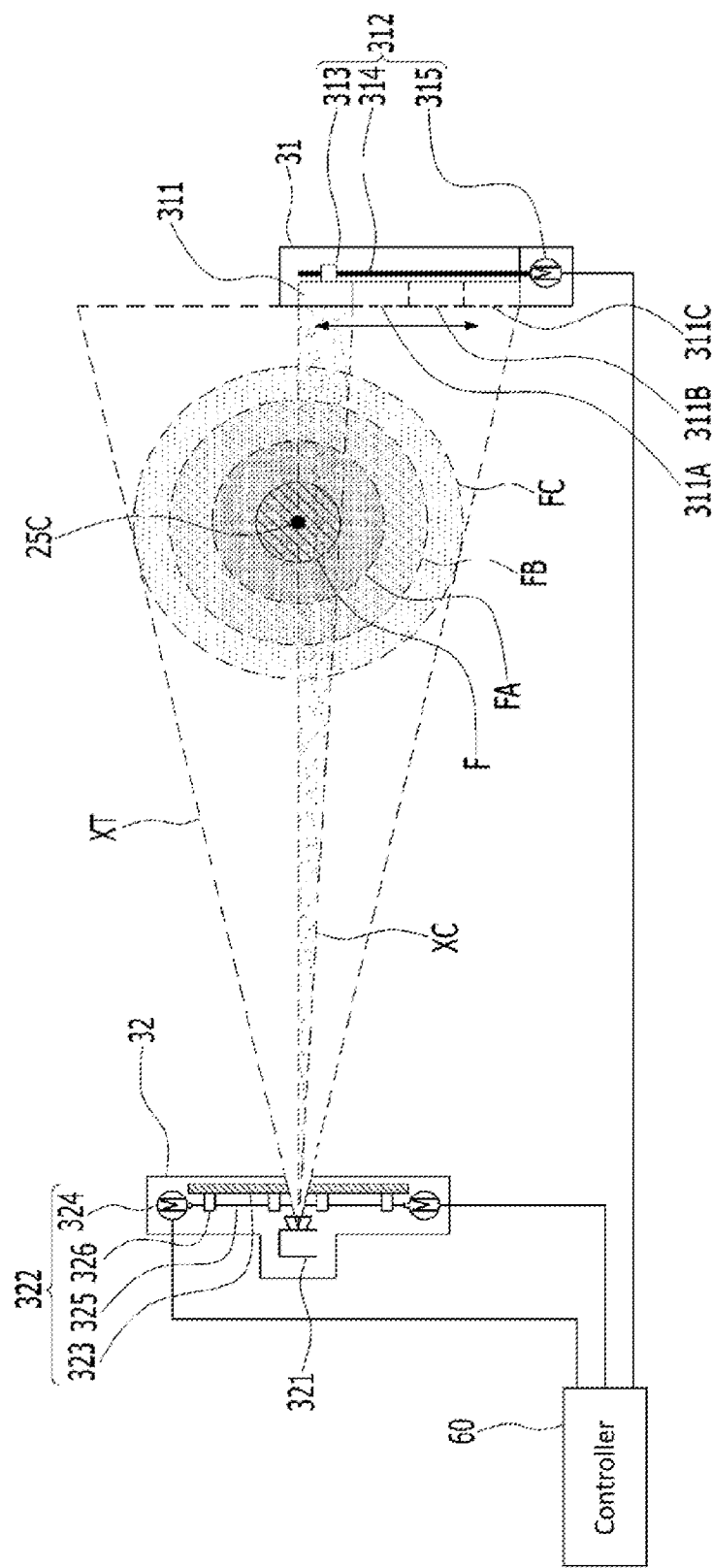
FIG. 5 shows a configuration that provides a wide radiographing target space provided by an X-ray sensor of the radiographing unit of the X-ray radiographing apparatus according to one embodiment of the present invention.

FIG. 5 shows a configuration that provides a wide radiographing target space provided by an X-ray sensor of the radiographing unit of the X-ray radiographing apparatus according to one embodiment of the present invention.

The present figure schematically shows the configuration of the radiographing unit of the X-ray radiographing apparatus, and is a schematic representation of the rotation axis 25C of the rotary arm 30 as viewed from above. The radiographing unit receives a control signal from the controller 60 and performs X-ray CT radiographing sequences. While performing X-ray CT radiographing sequences, the radiographing unit rotates a radiation path of an X-ray beam that passes a part of a target, and at the same time, moves a virtual X-ray beam center such that the X-ray beam is radiated at various angles over a predetermined range with respect to all parts within a radiographing target area.

A sensor unit 31 includes an X-ray sensor 311 oriented toward the generator unit 32. Herein, assuming that the height and the width of the entire area of the radiographing target area to obtain the CT image thereof are t1 and w1, respectively, the height t2 of the X-ray sensor is equal to or greater than magnification*first height t1 (($t2 \geq$ magnification*t1), and the width w2 of the X-ray sensor is less than magnification*first wide w1/2 (w2<magnification*w1/2). As reference, the height of the X-ray sensor may be adjusted according to the purpose. Based on a dental x-ray apparatus, in one embodiment, the width of the X-ray sensor may be 5~50 mm. In addition, the X-ray sensor 311 may move along a rotation track of the sensor unit 31 centered on the rotation axis 25C, for example, along a tangential direction of a circular trajectory. The generator unit 32 emits an X-ray beam XC aimed on the X-ray sensor 311 by interlocking with the movement of the X-ray sensor 311.

In the present figure, concentric circles F, FA, FB, and FC which are centered on the rotation axis 25C indicate the expansion of the radiographing target area according to the movement of the X-ray sensor 311. For example, when the X-ray sensor 311 is fixed on an initial position that is shown with the solid line and rotates over a predetermined angle, for example, 360 degree, an X-ray CT radiograph of the smallest radiographing target area FF may be obtained. This is substantially similar to a conventional half-beam x-ray radiographing apparatus. In addition, when an X-ray sensor 311 moves in the tangential direction by, for example, a width 311A from the position indicated by the solid line while performing successive X-ray radiographing accompanied by additional rotation centered on the rotation axis 25C, the radius of the radiographing target area FA is extended by the width 311A of the X-ray sensor 311. Similarly, when the X-ray sensor 311 moves by twice the width 311B and moves by three times the width 311C during successive radiographing, the radiographing target areas FB and FC are also expanded with the increase of the moving range. Therefore, the width of the X-ray sensor 311 is smaller than a value obtained by multiplying the radius of the extended actual radiographing target areas FA, FB, and FC by the maximum enlargement ratio.

As reference, in the above description, the X-ray sensor 311 is described as gradually moving according to a rotation cycle centered on the rotation axis 25C for convenience of explanation. Preferably, the X-ray sensor 311 may simultaneously move and rotate centered on the rotation axis 25C. The above process will be described hereinafter.

In terms of a device configuration, the sensor unit 31 includes an X-ray sensor driver 312 that moves the X-ray sensor 311 in the tangential direction of its rotation track within a limited range. The X-ray sensor driver 312 may include, for example, a motor 315 that generates driving power, a driving shaft 314 that transfers the generated driving power, and a connector 313 connecting a part of the X-ray sensor 311 and the driving shaft 314. However, such a mechanical configuration is merely an example, and it may be implemented in various forms.

Meanwhile, the generator unit 32 radiates an aimed X-ray beam XC on the X-ray sensor 311 by interlocking with the positional movement of the X-ray sensor 311, and has a width capable of covering the width of the X-ray sensor 311. As an example configuration for this, the generator unit 32 may include an X-ray generator 321 that emits an X-ray beam XT with a wide-width covering the moving range of the X-ray sensor 311, and a collimator 322 that emits an X-ray beam XC focused on the X-ray sensor 311 according to the position of the X-ray sensor 311 and having a narrow width associated with the X-ray sensor 311 by adjusting the wide-width X-ray beam XT. The collimator 322 may include at least one blade 323 that partially blocks the X-ray beam, a motor 324 that generates driving power to move the at least one blade 323, a driving shaft 325 that transfers the generated driving power, and a connector 326 that connects the blade 323 and a part of the driving shaft 325. The collimator 322 may drive a single blade that includes a slot with a predetermined width, and passes the focused X-ray beam XC by using a single motor, or may drive at least two blades by using respective motors.

However, the configuration of the generator unit 32 described above is merely an example, and may be implemented in various forms. For example, the generator unit 32 may include X-ray generator that emits an X-ray beam having a narrow width corresponding to the X-ray sensor 311, and adjusts the radiation direction of the X-ray beam emitted from the X-ray generator by interlocking with the positional movement of the X-ray sensor 311. Thus, a focused X-ray beam is emitted. Various other configurations are possible.

Meanwhile, the X-ray radiographing unit according to the embodiment described above may further include a controller 60 that is connected to the generator unit 32 and the sensor unit 31, and controls the same such that the generator unit 32 emits an X-ray beam XC that is focused on the X-ray sensor 311 by interlocking with the positional movement of the X-ray sensor 311. In detail, the controller 60 is connected to the X-ray sensor driver 312 to control the motor 315, and controls the direction of the X-ray beam that is emitted from the generator unit 32 by using a control signal of the motor 315 or a feedback reception signal of positional information of the X-ray sensor 311. The direction of the X-ray beam may be controlled by controlling the motor 324 that drives the collimator 322 as shown in the figure of the embodiment. However, as described above, when the generator unit 32 is implemented in a different form, the specific object that receives the control signal of the controller 60 may vary.

The present figure is the representation of the rotation axis 25C as viewed from above, and does not show vertical tilting of the sensor unit 31 or the X-ray generator 321. However, the sensor unit 31 and the X-ray generator 321 may be arranged to be inclined with respect to the rotation axis 25C as the sensor unit 31T and the X-ray generator 321T shown in FIG. 3. This feature will be the same in the following drawings.

Figure 6:
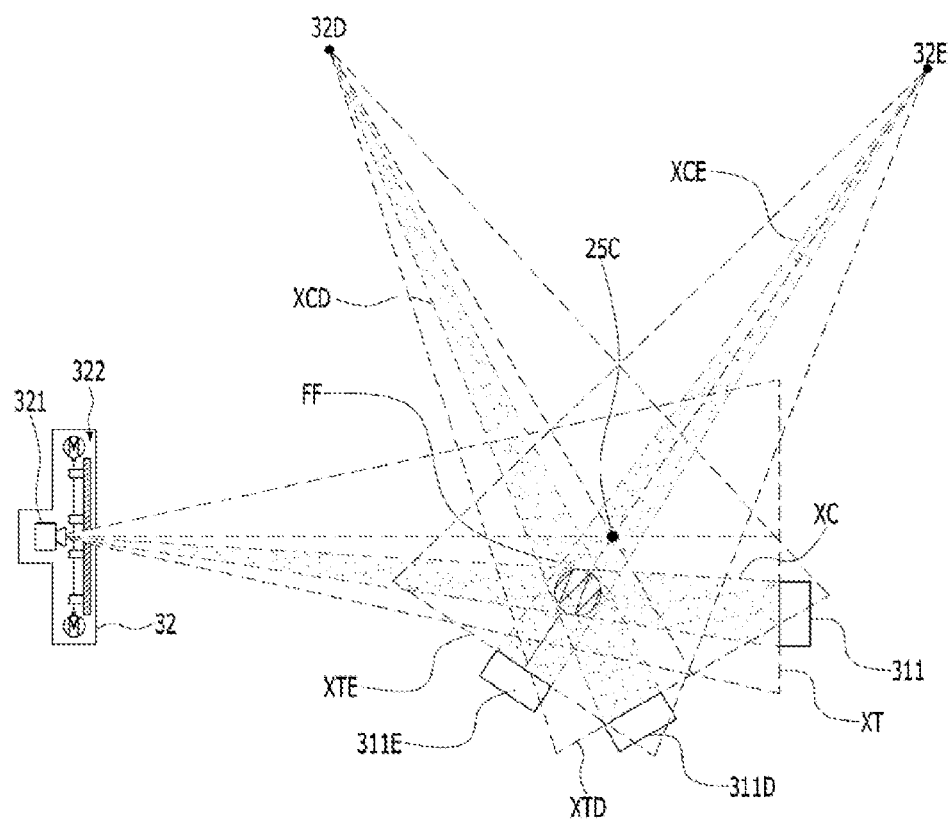
FIG. 6 shows a principle of radiographing a part of the radiographing target area by the radiographing unit of the X-ray radiographing apparatus according to one embodiment of the present invention.

FIG. 6 shows the principle of radiographing a part of the radiographing target area by the radiographing unit of the X-ray radiographing apparatus according to one embodiment of the present invention.

By using the X-ray radiographing unit of the embodiment of the present invention described with reference to FIG. 5, a radiographing target area described above is expanded, and a position of the radiographing target area may be freely selected and radiographed within the available range of the sensor 311. Of course, the position may be expanded by moving the sensor 311 based on the selected position.

The present figure shows wide-width X-ray beams XT, XTD, and XTE at some points 32D and 32E on a track along which the generator unit 32 passes, focused narrow X-ray beams XC, XCD, and XCE, and a radiographing target area FF formed at a position at which the X-ray beams overlap each other during radiographing by rotating the sensor unit including the generator unit 32 and the sensor 311 around the rotation axis 25C. When the generator unit 32 is positioned in some points 32D and 32E described above, the sensor 311 may receive the aimed X-ray beams XC, XCD, and XCE by moving to the associated points 32D and 32E within the radiation ranges of the wide-width X-ray beams XT, XTD, and XTE.

Figure 7:
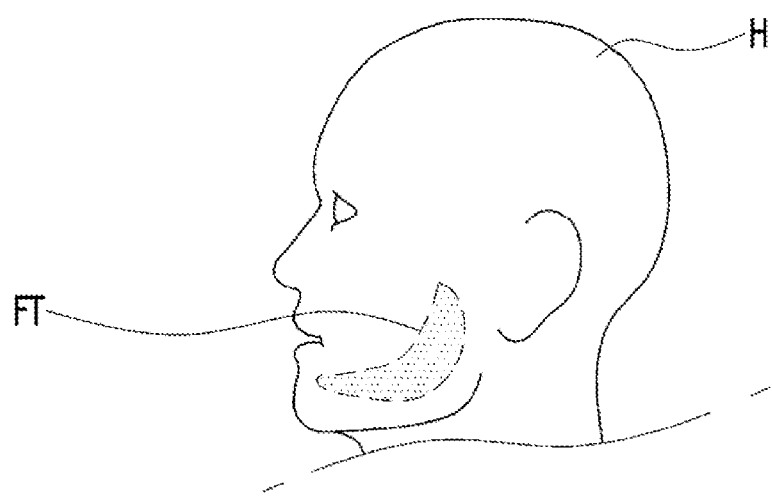
FIG. 7 shows an example of an atypical radiographing target space that may be radiographed by the X-ray radiographing apparatus according to one embodiment of the present invention.

FIG. 7 shows an example of an atypical radiographing target space that may be radiographed by the X-ray radiographing apparatus according to one embodiment of the present invention.

As shown in the figure, the shape of the radiographing target area FT is not limited to a cylindrical shape or the like. Free-form atypical radiographing target areas may be radiographed when the areas are expressed as formulas. The radiographing target area may be input using an input means before X-ray CT radiographing. However, various radiographing target areas corresponding to a plurality of clinically frequently utilized anatomical regions may be stored in advance and displayed to a user, and the user may perform input by selecting one of them.

Figure 8:
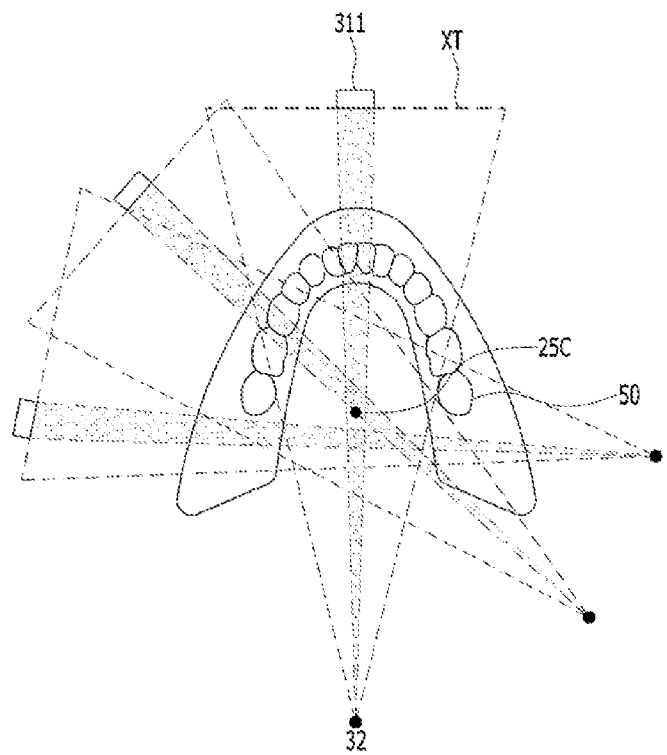
FIG. 8 shows a situation where a panoramic radiograph is radiographed by using the X-ray radiographing apparatus according to one embodiment of the present invention.

FIG. 8 shows the situation where a panoramic radiograph is radiographed by using the X-ray radiographing apparatus according to one embodiment of the present invention.

As shown in the figure, it is possible to obtain the same effect as moving a rotation axis in a conventional panoramic X-ray radiographing apparatus without actually moving the rotation axis 25C by rotating a sensor unit including the generator unit 32 and the sensor 311 and by moving a position of the sensor 311 to the tangential direction of the rotation track thereof. Accordingly, with the X-ray radiographing apparatus according to the present invention, X-ray CT radiographs, 3D radiographs, and panoramic X-ray radiographs for a focus layer corresponding to a dental arch 50 may be provided using such features.

Figure 9:
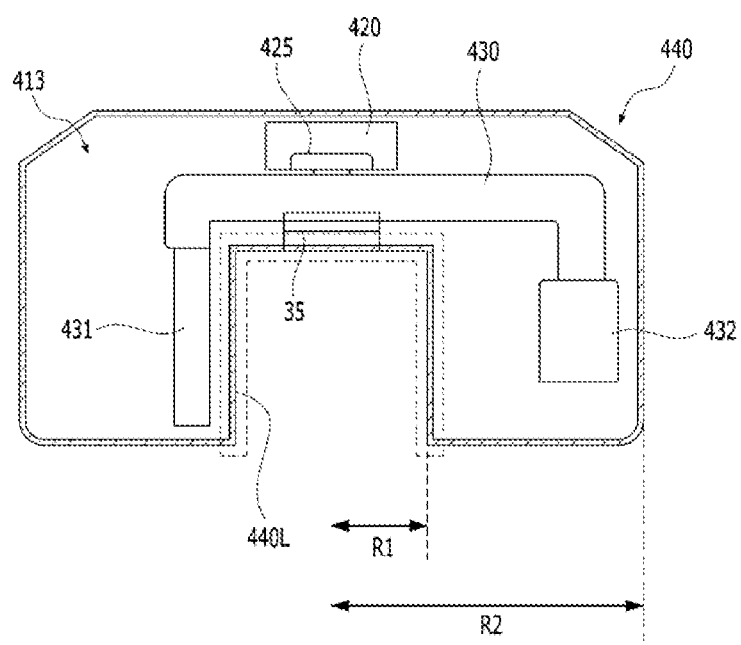
FIG. 9 schematically shows the inside of a radiographing housing of a dental X-ray radiographing apparatus according to one embodiment of the present invention.

FIG. 9 schematically shows the inside of a radiographing housing of a dental X-ray radiographing apparatus according to one embodiment of the present invention.

As shown in the figure, the X-ray radiographing apparatus according to one embodiment of the present invention includes a radiographing housing 440 that accommodates a radiographing unit 413. The radiographing housing 440 includes an X-ray generator 432 and an X-ray sensor 431 that are respectively arranged on both sides thereof, and covers a rotation area of a rotary arm 430 that is supported by a cantilever 420 so that the rotary arm 430 rotates around a rotation axis. A rotation driver 25 that makes the rotary arm 430 rotate with respect to the cantilever 420 may be installed in the cantilever 420 or inside the rotary arm 430.

The radiographing housing 440 is arranged below the rotary arm 430, and includes a radiographing housing lower casing 440L in which an inner diameter R1 thereof is smaller than a radius of rotation of the X-ray sensor 431 having a relatively small turning radius. The radiographing housing 440 may include various parts such as a radiographing housing lower casing 440L, described above, and an upper casing in which an outer diameter R2 thereof is larger than the radius of rotation of the X-ray generator 432 and which covers the remaining parts. There is no restriction on a boundary position between the upper casing and the lower casing 440L.

The radiographing housing 440 may be configured with a plastic structure such as ABS resin, carbon resin, etc. Since the size thereof is large and rotating components are provided therein, deformation such as deflection or vibration may occur. A part of the radiographing housing 440 lying on an upper part of the rotary arm 430 is supported by the cantilever 420, which is a fixed structure to support a load of the part, or may be supported by being connected to another fixed structure that is not shown, such as column. However, since the radiographing housing lower casing 440L that is positioned in a lower part of the rotary aim 430 is far from the fixed structure such as the cantilever 420, an elastic deflection or a permanent deflection caused by a creep may occur. In order to reinforce the structural rigidity and prevent the deflection thereof, the size and the self-load of the radiographing housing 440 may be increased.

According to the embodiment of the present invention, by using a rotation support 35 that is installed between a lower part of a rotation axis of the rotary arm 430 and the lower casing 440 of the radiographing housing 440, at least a part of a load of the radiographing housing 440, which is a non-rotating structure, may be supported by the rotary arm 430, which is a rotating structure. The load of the radiographing housing 440 transferred to the rotary arm 430 is transferred to the cantilever 420, and the load is supported by the cantilever 420 with the load of the rotary arm 430 itself. In other words, the rotation support 35 is connected to the lower part of the rotation axis of the rotary arm 430, which is a rotating structure, on one side thereof, and is connected to the lower casing 440L of the radiographing housing 440 on another side thereof. Thus, the rotary arm 4 may freely rotate while supporting a load in the axial direction of the radiographing housing 440. For this, the rotation support 35 may include a bearing disposed between the rotary arm 430 and the radiographing housing 440.

Figure 10:
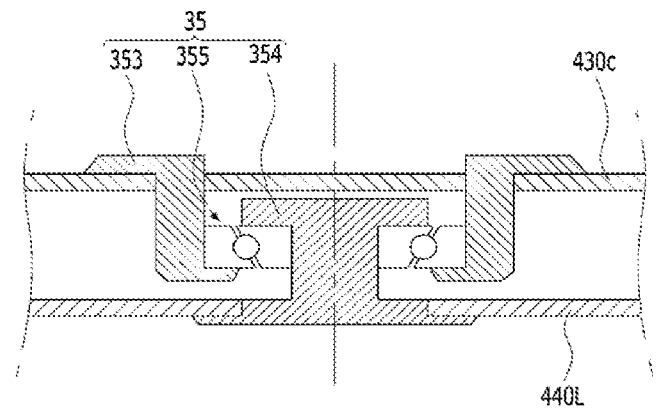
FIG. 10 shows an example of a rotation support disposed between a rotary arm and the radiographing housing of the embodiment of FIG. 9.

FIG. 10 shows an example of a rotation support disposed between the rotary arm and the radiographing housing of the embodiment of FIG. 9.

As shown in the figure, in one embodiment, the rotation support 35 may include a first bracket 353 that is installed in an lower part of the rotation axis of the rotary arm 430 and rotates with the rotary arm 430, a second bracket 354 that is installed inside the radiographing housing 440 close to the first bracket 353, and a bearing 355 that is installed between the first bracket 353 and the second bracket 354 so that the load of the radiographing housing 440, which is a non-rotating structure, is supported by the rotary arm 430, which is a rotating structure. Referring to the present figure, a part of the load of the radiographing housing 440, particularly, a load of a part including the lower casing 440L is transferred to an inner race of the bearing 355 through the second bracket 354, and then the load is transferred to an outer race of the bearing 355 through an inside of the bearing 355 such as ball, etc., and the load is then transferred to the rotary arm casing 430C through the first bracket 353. Herein, the load is transferred to the rotary arm casing 430C, but the load may be transferred to the frame structure of the rotary arm.

Herein, the bearing 355 may be selected from various types of bearings such as a ball bearing, a roller bearing, a radial bearing, a thrust bearing, etc. In one embodiment, an angular ball bearing may be selected for the bearing 355 such that the rotary aim 430 supports the load of the radiographing housing 440 due to gravity, and a load in a direction perpendicular to an axis.

Figure 11:
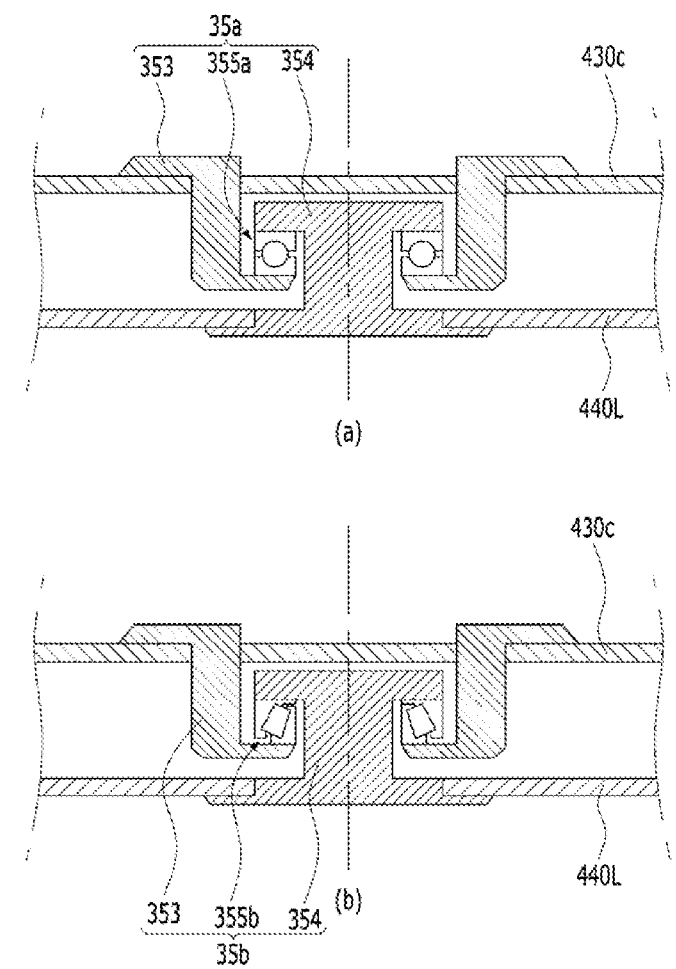
FIG. 11 shows another example of the rotation support of the embodiment of FIG. 9.

FIG. 11 shows another example of the rotation support of the embodiment of FIG. 9.

The rotation supports 35a and 35b that are shown in the present figure are the same as the rotation support 35 shown in FIG. 10 except for bearings 355a and 355b. FIG. 11(a) shows an example of selecting a thrust ball bearing for the bearing 355a of the rotation support 35a, and the example is focused on supporting a strong axial load. FIG. 11(b) shows an example of selecting a taper roller bearing for the bearing 355b of the rotation support 35b, the example is focused on supporting both a load in the axial direction and a load in the direction perpendicular to the axis, as in the example of FIG. 10. Accordingly, when a bearing that supports loads other than the axial direction is selected, it is advantageous to prevent deformation and vibration of the radiographing housing even in the case of abnormal shocks in a direction different from gravity such as when a body part of the examinee hits the radiographing housing.

Meanwhile, in the above description, the cantilever 420 and the radiographing housing 440 are described as non-rotating structures, but this does not mean that the cantilever 420 and the radiographing housing 440 are absolutely fixed structures with respect to the ground. It means that the cantilever 420 and the radiographing housing 440 are relatively fixed structures relative to the rotation movement of the rotary arm 430. Accordingly, when the cantilever 420 vertically moves with respect to a column fixed on the ground, the radiographing housing 440 also vertically moves. In addition, when the rotation axis of the rotary arm 430 moves along a straight track with respect to the cantilever 420 when radiographing panoramic X-ray radiograph, the radiographing housing 440 may be supported by moving with the rotation axis. The above feature may be also shown when the rotation axis moves two-dimensionally.

INDUSTRIAL APPLICABILITY

The present invention may be used mainly in the field of an x-ray diagnostic apparatus, such as a dental x-ray diagnostic apparatus, in which a head portion of a body is used as a target.

The invention claimed is:

1. A dental X-ray radiographing apparatus, the apparatus comprising:
a radiographing unit including an X-ray generator and an X-ray sensor that rotate about a vertical rotation axis and a target interposed therebetween, a rotary arm connecting the X-ray generator and the X-ray sensor to each other, and a rotation driver rotating the rotary arm about the rotation axis; and
a radiographing housing providing a radiographing space receiving at least a part of the target therein and covering the radiographing unit,
wherein the radiographing housing includes:
a lower part configured to be opened in order to provide a radiographing space; and
an upper part configured to be closed in order not to show a configuration and a movement of the radiographing unit.

2. The apparatus of claim 1, wherein the X-ray sensor is inclined with respect to the rotation axis such that a distance between the X-ray sensor and the rotation axis increases along a downward direction.

3. The apparatus of claim 2, wherein the X-ray sensor moves in a tangential direction of a rotation track centered on the rotation axis during X-ray radiographing.

4. The apparatus of claim 1, further comprising: a lifter that moves the radiographing unit and the radiographing housing upward and downward.

5. The apparatus of claim 4, further comprising: a handle frame disposed at a lower part of the radiographing housing with a variable height.

6. The apparatus of claim 5, wherein the target is a head of an examinee, and the apparatus further comprises: a chin rest disposed on the handle frame to support a chin of the examinee.

7. The apparatus of claim 6, wherein a height of the radiographing unit relative to the chin rest during X-ray radiographing is constant.

8. The apparatus of claim 7, further comprising: a displacement measuring unit measuring a height of the handle frame; and a controller controlling a vertical movement of the lifter according to the height of the handle frame.

9. The apparatus of claim 5, further comprising: a positioning guide disposed on the handle frame to support the target, and the positioning guide being entirely or partially received inside the radiographing space during X-ray radiographing.

10. The apparatus of claim 5, further comprising: at least one camera installed on the handle frame and imaging the target.

11. The apparatus of claim 1, further comprising: at least one camera installed in the radiographing housing and imaging the target.

12. The apparatus of claim 1, further comprising: a rotation support connecting the rotary arm and the radiographing housing.

13. The apparatus of claim 12, wherein the rotation support includes a bearing disposed between the rotary arm and the radiographing housing.

14. The apparatus of claim 12, wherein the rotation support further includes: a first bracket connected to the rotary arm and rotating therewith; and a second bracket connected to the radiographing housing with a bearing therebetween.

15. The apparatus of claim 1, wherein a radius of rotation of the X-ray sensor is smaller than a radius of rotation of the X-ray generator.

\* \* \* \* \*